(12) United States Patent
Butler et al.

(10) Patent No.: US 11,337,844 B2
(45) Date of Patent: May 24, 2022

(54) MOBILITY ENHANCEMENT DEVICE FOR ATTACHMENT TO FOOT OR FOOTWEAR

(71) Applicants: Saprina Renee Butler, Beebe, AR (US); Tessa Renee Butler, Beebe, AR (US)

(72) Inventors: Saprina Renee Butler, Beebe, AR (US); Tessa Renee Butler, Beebe, AR (US)

( * ) Notice: Subject to any disclaimer, the term of this patent is extended or adjusted under 35 U.S.C. 154(b) by 107 days.

(21) Appl. No.: 15/841,159

(22) Filed: Dec. 13, 2017

(65) Prior Publication Data

US 2019/0175379 A1 Jun. 13, 2019

(51) Int. Cl.
| | |
|---|---|
| *A61F 5/01* | (2006.01) |
| *A43B 7/1415* | (2022.01) |
| *A47B 91/06* | (2006.01) |
| *A61G 7/10* | (2006.01) |
| *A61G 7/053* | (2006.01) |

(52) U.S. Cl.
CPC .......... *A61F 5/0127* (2013.01); *A43B 7/1415* (2013.01); *A47B 91/06* (2013.01); *A61G 7/1026* (2013.01); *A61G 7/053* (2013.01); *A61G 7/1036* (2013.01)

(58) Field of Classification Search
CPC .................. A61F 5/0111; A61F 5/0127; A61F 2005/0172; A61F 2005/0197; A61F 13/064; A61F 13/065; A61F 13/067; A61F 13/068; A61F 13/069; A43B 7/14; A43B 7/1405; A43B 7/1415; A43B 7/142; A43B 7/1425; A43B 7/143; A43B 7/1435; A43B 7/1445; A43B 7/24; A43B 7/149; A43B 5/005; A43C 19/00; A43C 13/12
USPC ..... 128/845, 878, 882, 881; 36/22 A, 23, 90
See application file for complete search history.

(56) References Cited

U.S. PATENT DOCUMENTS

| | | | | |
|---|---|---|---|---|
| 4,774,776 | A * | 10/1988 | Gulli | A43B 13/203 36/7.8 |
| 5,081,740 | A * | 1/1992 | Smith | A47B 91/06 16/42 |
| 8,701,310 | B1* | 4/2014 | Walsh | A43B 3/16 36/7.4 |
| 2005/0251073 | A1* | 11/2005 | Roth | A61F 5/30 602/8 |
| 2017/0056251 | A1* | 3/2017 | Mack | A61F 13/063 |

* cited by examiner

*Primary Examiner* — Alireza Nia
*Assistant Examiner* — William T Kao
(74) *Attorney, Agent, or Firm* — Precipice IP PLLC; Angela Grayson

(57) ABSTRACT

A mobility enhancement device has an elongate strap of flexible material and a slide member having an inner face secured to a first surface of the strap and an outer smooth surface configured for sliding engagement with a floor surface. The strap is secured in a loop about a user's foot or footwear with releasable fastener devices associated with opposite end portions of the strap secured together and the slide member positioned to face downward from a ventral region of the sole of the foot or footwear so that the outer smooth surface is positioned for sliding engagement with a floor surface during ambulation or transfer.

13 Claims, 4 Drawing Sheets

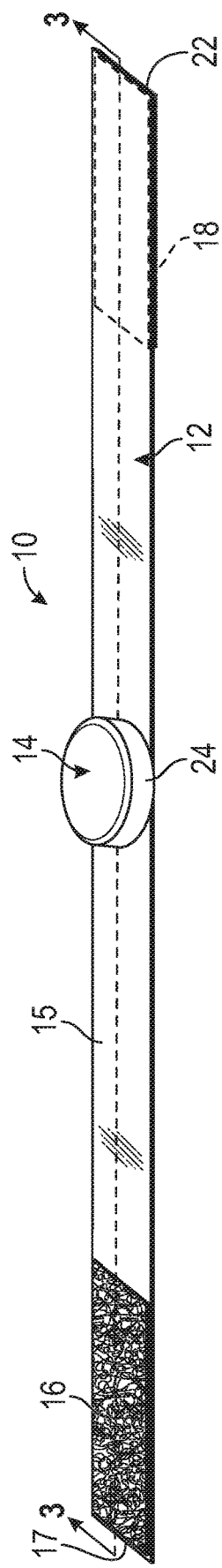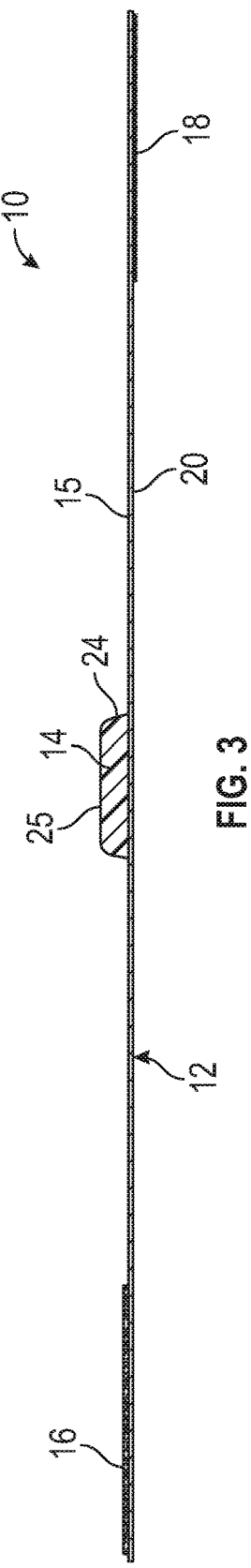

MOBILITY ENHANCEMENT DEVICE FOR ATTACHMENT TO FOOT OR FOOTWEAR

BACKGROUND

1. Field of the Invention

This invention relates generally to a mobility enhancement device for patient transfer and ambulation which is attached to a patient's footwear or directly to the foot and which is designed to allow the foot to glide or slide in order to increase mobility for those who find it difficult or impossible to lift one or both of their lower limbs from the ground due to leg muscle damage, injury, or other problems.

2. Related Art

When a person has an impaired lower limb, or two impaired lower limbs, they have reduced mobility. If the individual is unable to support their own body weight, caregivers often have difficulty in moving or transferring such individuals from a bed to a wheelchair, wheelchair to bed, wheelchair to toilet or shower, wheelchair to vehicle, and the like. This results in injury and fall risks to both the individual concerned and the caregiver.

In some cases, moleskin bandages (see U.S. Pat. No. 3,255,748) are applied to the tips of a patient or individual's shoes to allow the feet to glide more easily. However, moleskin wears down quickly with use and is not transferable to another shoe. Such bandages also leave a sticky residue on the shoe which may be difficult to remove.

U.S. Pat. No. 6,567,997 describes a mobility assisting system primarily for use by hemiplegics including a seat which may have a built in commode, a series of poles and a pivot disc on which a patient places a foot in order to swivel while gripping the poles to transfer to and from a bed or wheelchair. This is primarily designed for independent use and does not assist in moving a foot from one location to another. It also does not allow for the individual to stand with their legs at a shoulder length apart for a sturdy and stable base during transfer. This does not permit any assisting personnel or caregivers to place one foot between the patient's feet for proper body mechanics during transfer.

SUMMARY

According to one aspect, a mobility enhancement device comprises an elongate band or strap of flexible material designed to be secured around a patient's foot or footwear, the strap having opposite first and second ends, a first or outer face and a second, opposite or inner face, and a smooth slide member secured to the outer face of the strap, the slide member having a smooth flat or convex, rounded outer slide surface designed for gliding or sliding engagement with a floor surface. The slide member may be similar to a furniture glider or slide and may be generally disc shaped in some embodiments, with a rounded peripheral edge and a flat or substantially flat outer slide surface, or may have a convex or part-spherical outer slide surface. The slide member may be formed of any suitable smooth-surfaced material such as plastic or metal, or may have an outer coating of a slick or glossy material to form a slide surface.

Suitable fastener devices are provided at or adjacent the ends of the strap so that a the strap can secured transversely in a loop around a patient's foot or footwear with opposite ends of the strap secured together with part of the strap extending cross the sole of a shoe or user's foot so that the slide member faces outwards from the sole to engage the ground or floor surface. In one embodiment, a first patch of hook and loop fastener material is secured to the outer face of the strap adjacent the first strap end, and a mating patch of hook and loop fastener material is secured on the inner face of the strap adjacent the second strap end, and the strap ends are overlapped and secured together with the slide member facing the floor.

The slide member may be positioned at any location along the length of the strap. In one embodiment, the slide member is located in a central region of the strap and the fastener devices are secured together across the top of the foot or footwear with the slide member suitably positioned at the sole of the foot or footwear. In another embodiment where hook and loop fastener strips are used to secure the ends of the strap together, the slide member may be positioned at or near to the second strap end, above the patch of hook and loop fastener material on the inner face of the strap. In this case, the central region of the strap extends over the top of the foot or footwear and the fastener devices are secured together under the sole at an appropriate position for the slide member. In the latter case, pressure of the slide member on the floor helps to hold the strap ends together.

The device is designed to be secured to the foot or footwear of a person with reduced mobility. One or two such devices may be used, depending on whether the person has reduced mobility in one or both legs. The device is particularly intended to be secured over the foot so that the slide member is positioned on the ventral side of the foot, centered about a point on the foot where the wearer's weight is distributed when propulsion begins.

Other features and advantages of the present invention will become more readily apparent to those of ordinary skill in the art after reviewing the following detailed description and accompanying drawings.

BRIEF DESCRIPTION OF THE DRAWINGS

FIG. 2 is a perspective view of the device of FIG. 1 with one end of the device detached from the other end and the device in a generally flat configuration prior to attachment to a foot or footwear;

FIG. 3 is a cross-sectional view on the lines 3-3 of FIG. 2;

DETAILED DESCRIPTION

Figure 1:
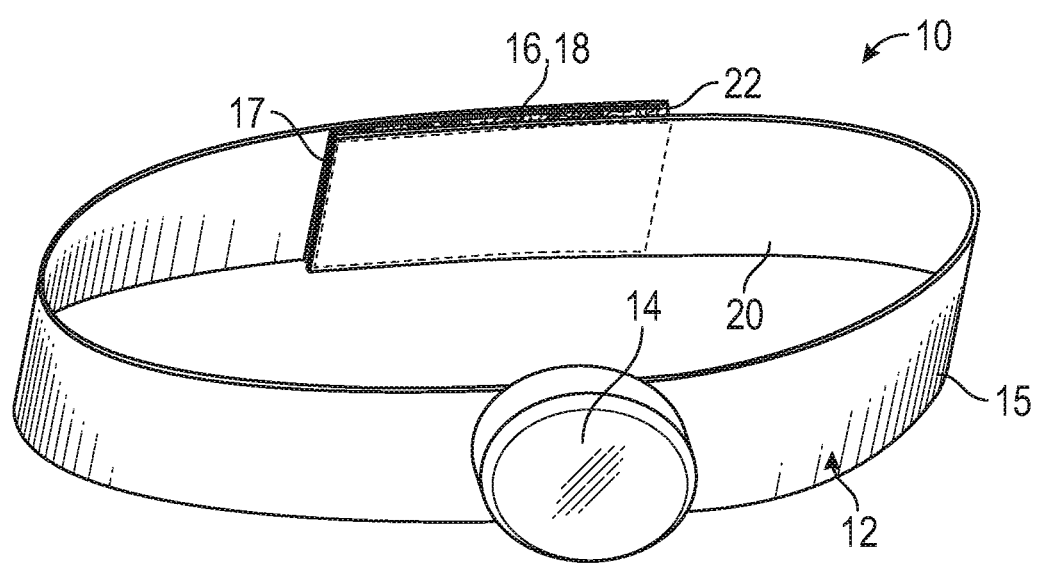
FIG. 1 is a perspective view of one embodiment of a mobility enhancement device secured in a loop configuration.

Certain embodiments as disclosed herein provide for a mobility enhancement device for attachment to a patient's footwear or directly to the foot and which is designed to allow the foot to glide or slide in order to increase mobility for those who find it difficult or impossible to lift one or both of their lower limbs from the ground due to leg muscle damage, injury, or other problems. In some embodiments, the device comprises a flexible strap having a slide member secured on one face of the strap, and releasable fastener devices at opposite ends of the strap for securing the strap about a wearer's foot or footwear with the slide member facing generally downwards towards a ground or floor surface when the device is in use.

After reading this description it will become apparent to one skilled in the art how to implement the invention in various alternative embodiments and alternative applications. However, although various embodiments of the present invention will be described herein, it is understood that these embodiments are presented by way of example only, and not limitation.

FIGS. 1 to 4 illustrate a first embodiment of a mobility enhancement device 10 which comprises an elongate band or strap 12, a slide member 14 secured at a generally central location on one face 15 of the strap, a first fastener device or strip 16 located on face 15 adjacent one end 17 of the strap, and a second fastener device or strip 18 which is releasably mateable with the first fastener device and is located on the opposite face 20 of the strap adjacent the second end 22 of the strap.

Figure 4:
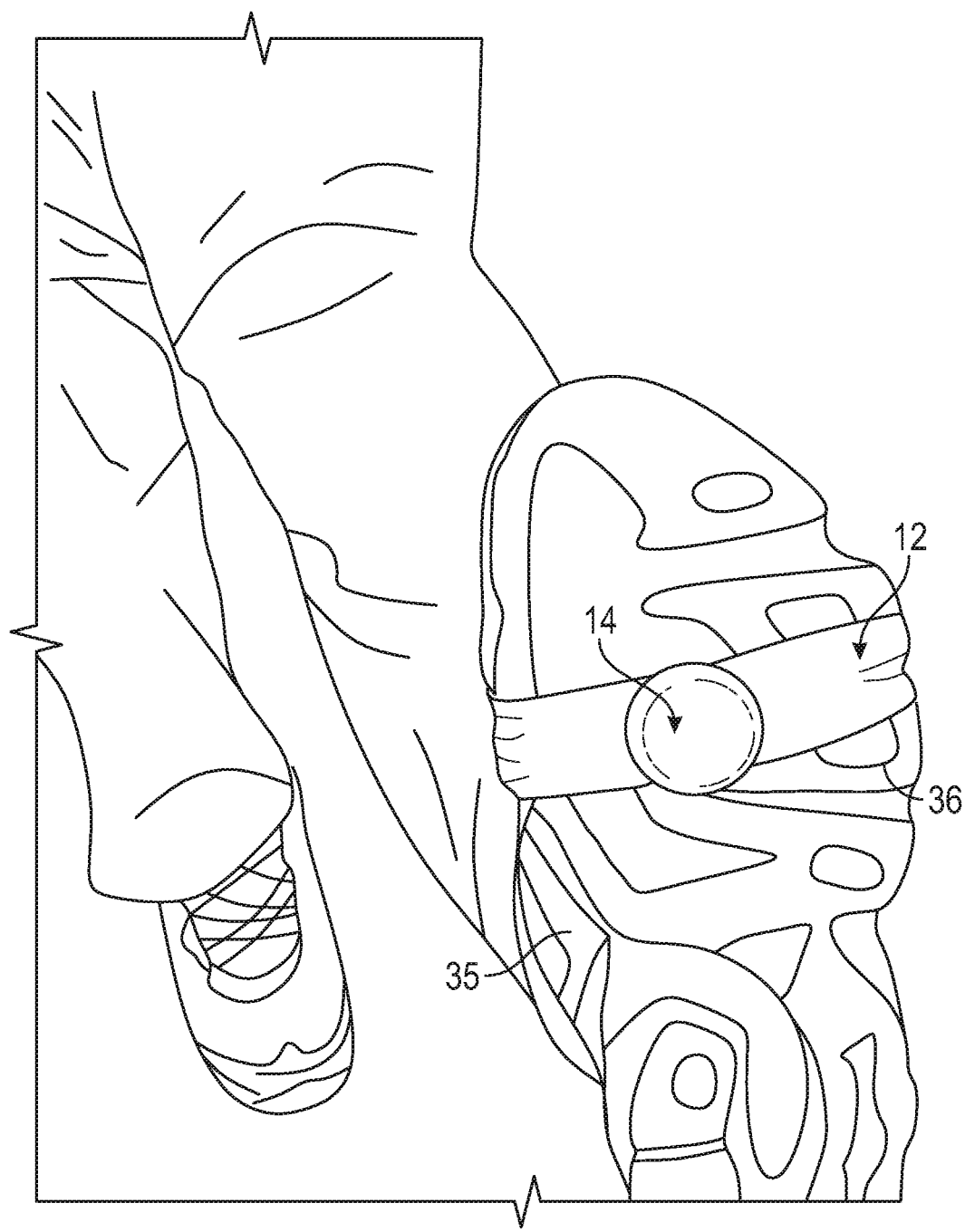
FIG. 4 illustrates the device of FIGS. 1 to 3 secured about a wearer's shoe with the slide member or slider in a suitable position to provide improved mobility.

In the illustrated embodiment, the mateable first and second fastener devices 16, 18 comprise mating strips of hook and loop fastener material such as VELCRO® secured to the strap via adhesive, heat bonding, stitching, or the like, but other types of adjustable strap fasteners may be provided in alternative embodiments, such as snap fasteners, buttons, buckles, and the like. The strap may be of any suitable flexible strap material and is of extendable or elasticated fabric or plastic material in some embodiments. Alternatively, the strap may be of non-elasticated material and the length when secured in a loop may be adjustable via a buckle or snap fastener. The strap is of sufficient length (when extended if the strap is of elasticated material) to be wrapped around a wearer's foot or footwear with the ends overlapped at the top of the foot or footwear, as illustrated in FIGS. 1 and 4. Different length straps may be provided for different size feet, such as children and adults.

Figure 5:
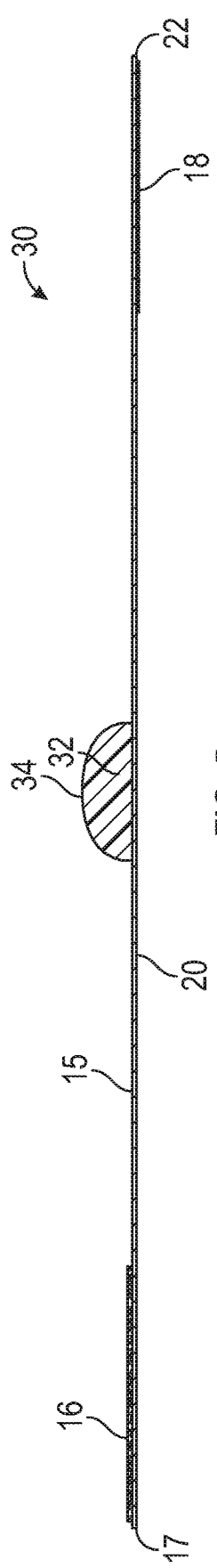
FIG. 5 is a cross-sectional view similar to FIG. 3 illustrating a second embodiment of a mobility enhancement device with a modified slider.
Figure 6:
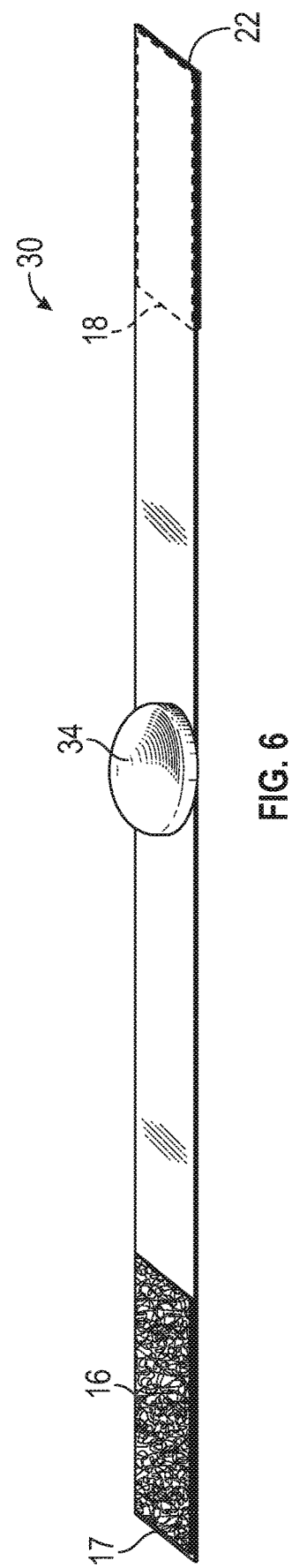
FIG. 6 is a top perspective view of the device of FIG. 5.

In some embodiments, the slide member 14 is similar to a furniture glider or slide and may be generally disc shaped, with a flat inner surface which is secured to the strap, a circular peripheral edge 24 and a flat or substantially flat outer slide surface 25. In the alternative embodiment of FIGS. 5 and 6, a mobility enhancement device 30 is provided which has a modified slide member 32 in place of slide member 14. Slide member 32 has a flat or relatively flat inner surface secured to the strap and a smooth, convex or part spherical outer slide surface 34. In one embodiment, the outer slide surface 34 is a part spherical surface of a sphere. Device 30 is otherwise identical to device 10 of FIGS. 1 to 4, and like reference numbers are used for like parts as appropriate. The slide member 14 or 32 may be formed of any suitable smooth-surfaced rigid material such as plastic or metal which is capable of sliding on a smooth or carpeted surface. In some embodiments, the outer surface of the slide member may have an outer coating of a slick or glossy material to form a slide surface. Slide member 14 or 32 may be secured to strap 12 by adhesive bonding, plastic welding (where both parts are of thermoplastic material), or the like.

In one example, strap 12 has a length of 11 inches and a width of 0.75 inches, and the fastener strips are of 2.5 inches in length. In one embodiment, slide member 14 has a diameter of around 1 to 1.25 inches and a height of 0.5 to 1 inch. Slide member 32 may be of similar dimensions. Other dimensions may be used in alternative embodiments.

FIG. 1 illustrates device 10 secured in a loop condition with strap end 22 overlapped with strap end 17 with the two fastener strips secured together in face-to-face engagement. FIG. 4 illustrates the strap in the loop configuration secured around a wearer's shoe 35 with the slide member 14 placed at a suitable position extending across the sole 36 of the shoe and opposite ends of the strap secured together across the shoe upper or upper top of the foot. Although the strap is shown positioned about a user's shoe in FIG. 4, it will be understood that the device may also be secured about a user's foot or sock if no shoe is worn. The slide member is secured in a ventral region of the sole of the foot or shoe, generally corresponding with the ball of the foot, or the part of the foot which first engages the floor during ambulation.

The mobility enhancement devices 10 and 30 increase mobility for individuals who are unable to lift one or both of their lower limbs off the ground using their own muscles. One or two such devices may be used by affected individuals or patients for both transfer and indoor ambulation. The device allows the patient to place his or her feet in any width or orientation. When the device is properly positioned on the foot or shoe, the slide member is located on the ventral side of the foot, centered about the point on the foot where the wearer's weight is distributed when propulsion begins. When this device is applied, the wearer is able to slide the flat or convex, part-spherical slide surface of the slide member across the floor surface in the direction of ambulation, without needing to use leg muscles to lift the foot. If the user is unable to support their own body weight during ambulation, a caregiver is able to slide the affected limb without loss of balance. The patient or user of the device may also turn the foot for transfer using the slide member, i.e. to transfer from wheelchair to bed or vice versa, wheelchair to toilet or vice versa, and the like, with or without hands on assistance of a caregiver (depending on patient mobility). Ideally, the patient stands with their legs a shoulder width apart, allowing the assisting personnel to place one foot between the patient's feet for proper body mechanics during patient transfer.

The slide member is designed for use on a relatively smooth floor surface such as a flat floor surface or a carpet surface with low tuft height. The device is readily transferrable from foot to foot or shoe to shoe without leaving any residue or marks on the shoe or foot, and has a longer wear and tear capability than moleskin.

In the above embodiments, the slide member 14, 32 is secured at a generally central position on the strap 12. However, it may be secured at different locations on the strap in alternative embodiments, with the user or caregiver securing the ends of the strap together at an appropriate location for positioning the slide member at the desired position in the ventral region of the sole of the shoe or footwear. In some embodiments, the slide member may be secured to the outer surface of the strap at a location overlying the fastener patch or strip 18 at end 22 of the strap. In this case, the central region of the strap extends over the top of the foot or footwear with the fastener strips overlapped and secured together at the sole so as to position the slide member as seen in FIG. 4.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encom-

We claim:

1. A propulsion mobility enhancement device, comprising:
an elongate strap of flexible material placed over the exterior of a user's footwear having opposite first and second surfaces and opposite first and second ends, wherein the first surface is outwardly facing towards a floor when worn by a wearer, and the second surface is inwardly facing towards a wearer's foot when worn by the wearer; a rigid slide member which is engaged only along a ventral region of the exterior sole of the footwear having a slide surface inner face secured to the outwardly facing first surface of the strap and a slide surface outer face configured for direct propulsive sliding engagement for sliding across a smooth or carpeted floor, and, wherein the slide member outer face further comprises a slick coating which forms a glide surface; and first and second releasable mateable fastener devices associated with the strap and configured for releasable mating engagement to secure the strap in a loop around the exterior of a user's footwear such that the loop positions the slide member along the ventral region along the exterior sole of the footwear with the slide member facing outwardly from the ventral region of the sole of the footwear.

2. The device of claim 1, wherein the slide member has a flat outer slide surface for sliding on a floor.

3. The device of claim 1, wherein the slide member has a convex outer slide surface for sliding on a floor.

4. The device of claim 3, wherein the outer surface is part-spherical.

5. The device of claim 1, wherein the inner face of the slide member is flat.

6. The device of claim 1, wherein the slide member is plastic or metal.

7. The device of claim 1, wherein the slide member is secured to the strap at a location spaced from the first and second ends of the strap.

8. The device of claim 7, wherein the slide member is secured at a central position on the strap.

9. The device of claim 1, wherein the strap is of elasticated, extendable material.

10. The device of claim 1, wherein the first fastener device comprises a strip of fastener material secured to the first surface of the strap adjacent the first end of the strap, and the second fastener device comprises a strip of fastener material secured to the second surface of the strap adjacent the second end of the strap, one of the strips comprising hook type fastener material and the other strip comprising mating loop type fastener material.

11. The device of claim 1 wherein the slide member has a circular peripheral edge.

12. A method of attaching a slide member to the sole of a patient's foot for enhancing propulsion mobility, comprising:
positioning a strap over the exterior of a user's footwear, wherein the strap is comprised of flexible material having opposite first and second surfaces and opposite first and second ends, wherein the first surface is outwardly facing towards a floor when worn by a wearer, and the second surface is inwardly facing towards the wearer's foot when worn by the wearer, wherein the strap is positioned in a loop around the exterior of a user's footwear such that the loop positions a rigid slide member along the ventral region along the exterior sole of the footwear and such that a slide member is secured only in the ventral region of the sole of the footwear; the slide member having a slide surface inner face secured to the outwardly facing first surface of the strap and a slide surface outer face configured for direct propulsive sliding engagement for sliding across a smooth or carpeted floor, wherein, the slide member outer face further comprises a slick coating which forms a glide surface, is secured to the strap and located in the ventral region along the sole of the footwear where the patient's weight is distributed at the start of propulsion, with a smooth outer slide surface of the slide member facing outwards from the sole of the footwear; and
securing opposite ends of the strap together to releasably fasten the slide member to the footwear; whereby the foot can be moved or rotated on a smooth floor surface using the slide member without lifting the foot from the floor surface to improve patient ambulation.

13. The method of claim 12, wherein the slide member is located in a central region of the strap, and the step of positioning the strap in a loop comprises positioning the central region of the strap to extend across the sole of the footwear and extending opposite ends of the strap over the top of the footwear, and securing opposite ends of the strap over the top of the footwear.

* * * * *